United States Patent [19]

Katz et al.

[11] Patent Number: 4,775,690

[45] Date of Patent: * Oct. 4, 1988

[54] SUBSTITUTED 1,3,4,9-TETRAHYDROPYRANO(3,4-B)INDOLE-1-ACETIC ACIDS

[75] Inventors: Alan H. Katz, Lawrenceville; Christopher A. Demerson, Plainsboro; Leslie G. Humber, North Brunswick, both of N.J.

[73] Assignee: American Home Products Corporation, New York, N.Y.

[*] Notice: The portion of the term of this patent subsequent to Jun. 2, 2004 has been disclaimed.

[21] Appl. No.: 2,825

[22] Filed: Jan. 13, 1987

[51] Int. Cl.⁴ .................. A61K 31/40; C07D 491/052
[52] U.S. Cl. ..................................... 514/411; 548/432
[58] Field of Search .......................... 548/432; 514/411

[56] References Cited

U.S. PATENT DOCUMENTS

| | | | |
|---|---|---|---|
| 3,843,681 | 10/1974 | Demerson et al. | 548/432 |
| 3,880,853 | 4/1975 | Demerson et al. | 548/432 |
| 3,939,178 | 2/1976 | Demerson et al. | 548/432 |
| 3,974,179 | 8/1976 | Demerson et al. | 548/432 |
| 4,003,913 | 1/1977 | Demerson et al. | 548/432 |
| 4,012,417 | 3/1977 | Demerson et al. | 548/432 |
| 4,021,451 | 5/1977 | Dobson et al. | 548/432 |
| 4,041,169 | 8/1977 | Demerson et al. | 514/411 |
| 4,066,779 | 1/1978 | Demerson et al. | 514/411 |
| 4,066,780 | 1/1978 | Demerson et al. | 514/411 |
| 4,070,371 | 1/1978 | Demerson et al. | 548/432 |
| 4,076,831 | 2/1978 | Demerson et al. | 548/432 |

OTHER PUBLICATIONS

Derwent Abstract of Netherlands Pat. No. 7300518, published Jul. 17, 1973.
H. Yale, J. Med. Pharm. Chem., vol. 1, No. 2, (1959), pp. 121-122, The Trifluoromethyl Group in Medicinal Chemistry.
A. Burger, Medicinal Chemistry, Third Edition, Part I, (1971), p. 71, Wiley-Interscience, N.Y.
Derwent Abstract of European Pat. No. 5365, published 11/1979.
Derwent Abstract of German Pat. No. DE 2301525, published 7/1973.

*Primary Examiner*—Mary E. Ceperley
*Attorney, Agent, or Firm*—Walter Patton

[57] ABSTRACT

Indole derivatives characterized by having a 1,3,4,9-tetrahydropyrano[3,4-b]indole-1-acetic acid nucleus bearing a substituent in position 1 and 4. The nucleus may be optionally substituted at positions 5, 6, 7 and 8. The derivatives are useful anti-inflammatory and analgesic agents and methods for their preparation and use are also disclosed.

3 Claims, No Drawings

SUBSTITUTED 1,3,4,9-TETRAHYDROPYRANO(3,4-B)INDOLE-1-ACETIC ACIDS

BACKGROUND OF THE INVENTION a. Field of Invention

This invention relates to novel indole derivatives, and to the processes for their preparation and use.

Notwithstanding the advances made during the last four decades in the development of agents for the treatment of pain-producing and inflammatory conditions, there still remains a need for effective agents without the side effects associated with the therapeutic agents presently used for this purpose.

More specifically, this invention relates to tricyclic acetic acid derivatives in which the tricyclic portion thereof is characterized by having an indole portion fused to a pyrano ring. Still more specifically, the compounds of this invention are characterized as derivatives of the following tricyclic acetic acid system:

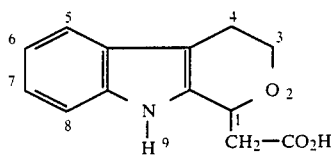

1,3,4,9-tetrahydropyrano[3,4-b]indole-1-acetic acid in which the carbons at the 1-, and 4-position, and optionally at the 5-, 6-, 7-, and 8-positions are further substituted.

The indole derivatives of this invention have been found to exhibit useful pharmacodynamic properties without eliciting undesirable side effects. Notable attributes of this effect are anti-inflammatory and analgesic activities.

b. Prior Art

The closest prior art to the present invention is:

Demerson et al, U.S. Pat. No. 3,939,178. Demerson et al disclosed 1,3,4,9-tetrahydropyrano[3,4-b]indoles and 1,3,4,9-tetrahydrothiopyrano[3,4-b]indoles having analgesic and anti-inflammatory activity but not with the substituents of the present invention. Related are U.S. Pat. Nos. 3,974,179 and 3,843,681.

SUMMARY OF THE INVENTION

The compounds of this invention are represented by formula (I)

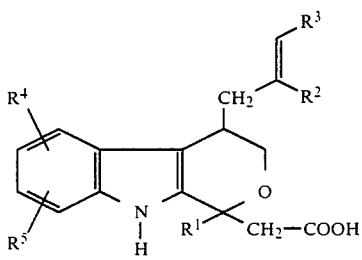

wherein $R^1$ is lower alkyl containing 1 to 4 carbon atoms, $R^2$ and $R^3$ are hydrogen or $R^2$ and $R^3$ are joined together to give

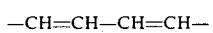

and form a benzene ring, $R^4$ and $R^5$ are hydrogen, alkyl containing 1 to 6 carbon atoms, halogen, and the pharmaceutically acceptable salts thereof.

A preferred aspect of the present invention is the series of compounds represented by formula (II).

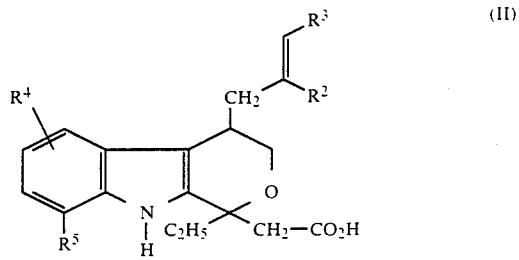

wherein $R^2$ and $R^3$ are hydrogen or $R^2$ and $R^3$ are joined together to give

and form a benzene ring, $R^4$ and $R^5$ are hydrogen, lower alkyl containing 1 to 4 carbon atoms, halogen and the pharmaceutically acceptable salts thereof.

A still further preferred aspect of the present invention is the compounds represented by formula (II) wherein $R^2$ and $R^3$ are hydrogen or $R^2$ and $R^3$ are joined together to give

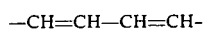

and form a benzene ring, $R^4$ is hydrogen, or 5-, 6-, or 7-halogen, $R^5$ is hydrogen, methyl, ethyl or propyl and the pharmaceutically acceptable salts thereof.

A further aspect of the present invention is the compounds represented by formula (XIV)

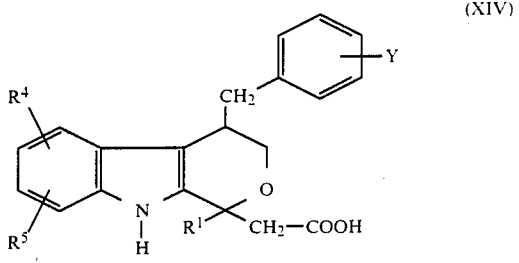

wherein $R^1$ is lower alkyl containing 1 to 4 carbon atoms, $R^4$ and $R^5$ are hydrogen, alkyl containing 1 to 6 carbon atoms or halogen, and Y is 4-halogen, 2- and 4-dihalogen, 3-trifluoromethyl, or 4-methyoxy and the pharmaceutically acceptable salts thereof.

The most preferred compounds of the present invention are designated 1-ethyl-1,3,4,9-tetrahydro-4-(phenylmethyl)-pyrano[3,4-b]indole-1-acetic acid;

7-chloro-1-ethyl-1,3,4,9-tetrahydro-8-methyl-4-(2-propenyl)-pyrano[3,4-b]indole-1-acetic acid;

1-ethyl-7-fluoro-1,3,4,9-tetrahydro-8-methyl-4-(2-propenyl)-pyrano[3,4-b]indole-1-acetic acid;

8-chloro-1-ethyl-1,3,4,9-tetrahydro-5-methyl-4-(phenylmethyl)-pyrano[3,4-b]indole-1-acetic acid;

1,8-diethyl-1,3,4,9-tetrahydro-4-(2-propenyl)-pyrano[3,4-b]indole-1-acetic acid;

1-ethyl-1,3,4,9-tetrahydro-8-methyl-4-(2-propenyl)-pyrano[3,4-b]indole-1-acetic acid;
7-chloro-1-ethyl-1,3,4,9-tetrahydro-4-(phenylmethyl)-pyrano[3,4-b]indole-1-acetic acid;
6-bromo-1-ethyl-1,3,4,9-tetrahydro-4-(phenylmethyl)-pyrano[3,4-b]indole-1-acetic acid;
5-chloro-1-ethyl-1,3,4,9-tetrahydro-8-methyl-4-(phenylmethyl)-pyrano[3,4-b]indole-1-acetic acid;
7,8-dichloro-1-ethyl-1,3,4,9-tetrahydro-4-(phenylmethyl)-pyrano[3,4-b]indole-1-acetic acid;
7-chloro-1-ethyl-1,3,4,9-tetrahydro-8-methyl-4-(phenylmethyl)-pyrano[3,4-b]indole-1-acetic acid;
1-ethyl-1,3,4,9-tetrahydro-8-methyl-4-(phenylmethyl)-pyrano[3,4-b]indole-1-acetic acid;
1-ethyl-1,3,4,9-tetrahydro-4-(2-propenyl)-8-propyl-pyrano[3,4-b]indole-1-acetic acid;
1,8-diethyl-1,3,4,9-tetrahydro-4-(2-propenyl)-pyrano[3,4-b]indole-1-acetic acid.

The indole derivatives of this invention of formula I are prepared by the following three processes.

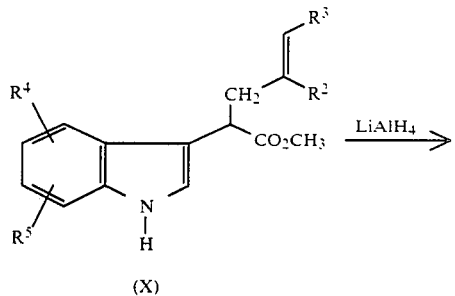

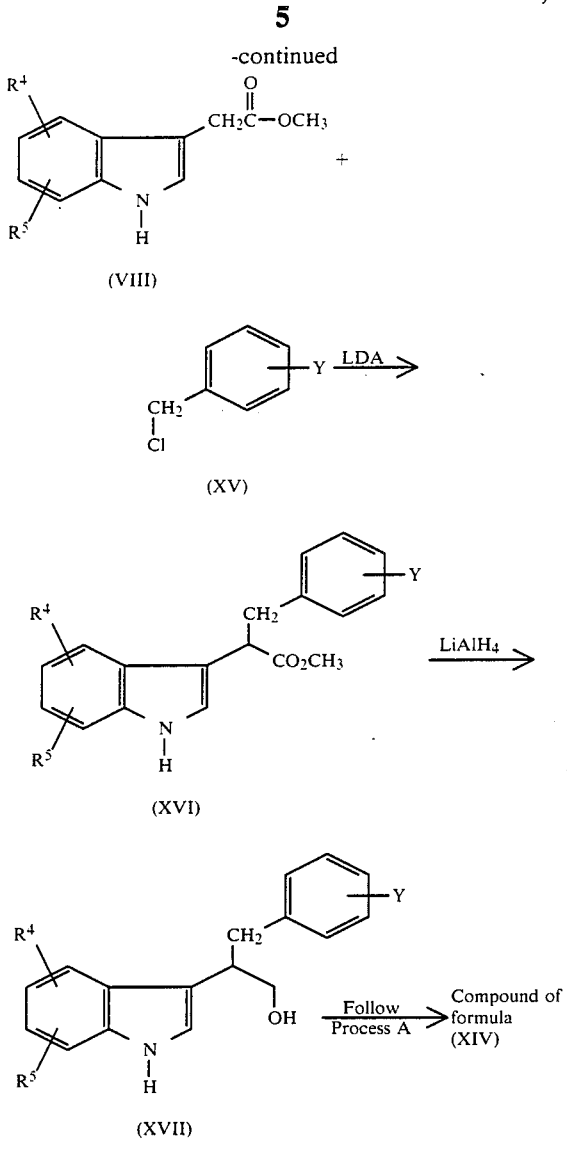

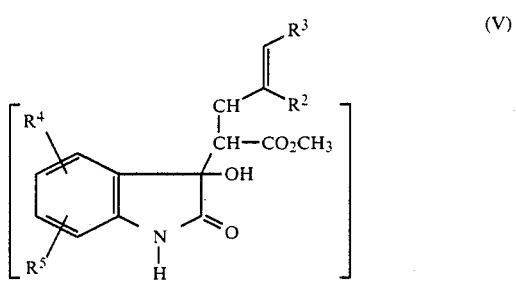

The intermediate (V), without isolation, is reduced using a hydride, for example LiAlH$_4$, to give the β-substituted tryptophol (VI), wherein $R^2$, $R^3$, $R^4$ and $R^5$ are as defined above. Reaction of the β-substituted tryptophol (VI) with 3-methoxy-2-alkanoic acid, methyl ester (VII), wherein $R^1$ is as defined in formula (I) and (II), in the presence of a Lewis acid, for example boron trifluoride etherate, followed by alkaline hydrolysis affords compounds of formula (I) and (II). Alternatively, condensation with a substituted β-keto ester, followed by hydrolysis, as described by Demerson et al. U.S. Pat. No. 3,939,178, affords compounds of formula (I) and (II).

Process A was used for the preparation of the compounds of Example 1 and 8–37, Table II. The required isatins III were prepared as described by Frank D. Popp, in Advances in Heterocyclic Chemistry, 18, pp 1–58 (1975).

Process B describes a process for preparing compounds of formula (I) and (II) which comprises alkylation of a substituted indole-3-acetic acid methyl ester VIII, wherein $R^4$ and $R^5$ are as defined in formula (I) and (II), with an organic halide (IX), wherein $R^2$ and $R^3$ are as defined in formula (I) and (II), to give the α-substituted indole-3-acetic acid ester (X), wherein $R^2$, $R^3$, $R^4$ and $R^5$ are as defined above. The ester (X) is reduced, for example with LiAlH$_4$, to afford the β-substituted tryptophol (VI), described in Process A above. The compound (VI) is converted to the compound of formula (I) and (II) by Process A described above.

Process B was used for the preparation of the compound of Example 2, Table II.

Process C describes a process for preparing compounds of formula (I) and (II) which comprises the reaction of a substituted indole (XI), wherein $R^4$ and $R^5$ are as defined in formula (I) and (II), and a substituted acid chloride (XII), wherein $R^2$ and $R^3$ are as defined in formula (I) and (II), affording the substituted 3-acylindole (XIII), wherein $R^2$, $R^3$, $R^4$ and $R^5$ are as defined above. Rearrangement of compound (XIII) to the intermediate α-substituted indole-3-acetic acid ester (X), described in Process B is accomplished using thallium (III) nitrate by a method of E. C. Taylor et al, J. Amer. Chem. Sec. 98, 3037 (1976).

Process C was used for the preparation of the compounds of Example 4 and 5, Table II.

Process D describes a process for preparing compounds of formula (XIV) which comprises alkylation of a substituted indole-3-acetic acid methyl ester VIII, wherein $R^4$ and $R^5$ are as defined in formula (XIV), with a substituted benzyl halide (XV), wherein X is as defined in formula (XIV), to give the α-substituted indole-3-acetic acid ester (XVI), wherein $R^4$, $R^5$ and X are as defined above. The ester (XVI) is reduced, for example with LiAlH$_4$, to afford the β-substituted tryptophol (XVII). The compound (XVII) is converted to the compound of formula (XIV) by Process A described above.

Process D was used for the preparation of the compounds 40 to 45 of Table II.

Alternatively, the process described in U.S. Pat. No. 4,585,877, may be adapted for the production of the compounds of the present invention of formula (I) and (II).

DETAILED DESCRIPTION OF THE INVENTION

The term "alkyl" as used herein represents straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "lower alkyl" as used herein represents straight chain alkyl radicals containing 1 to 4 carbon atoms and branched chain alkyl radicals containing three to four carbon atoms and includes methyl, ethyl, propyl, isopropyl, butyl, isobutyl and the like.

The term "halogen" as used herein includes fluorine, chlorine, bromine and iodine.

The compounds of formula (I) form salts with suitable pharmaceutically acceptable inorganic and organic bases. These derived salts possess the same activities as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. The preferred salt is the sodium salt. Suitable organic bases include the following amines; lower mono-, di- and tri-alkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethyl-piperidinium salts, which are characterized by good water-solubility. In principle, however, there can be used all the ammonium salts which are physiologically compatible.

The transformations to the salts can be carried out by a variety of methods known in the art. For example, in the case of salts of inorganic bases, it is preferred to dissolve the acid of formula (I) in water containing at least one equivalent amount of a hydroxide, carbonate, or bicarbonate. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid salt if that form is desired.

To produce an amine salt, the acid of formula (I) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Included in the present invention are the diastereoisomers wherein the 4-substituent is either cis or trans to the acetic acid chain at position one.

Also included in this invention are the optical isomers of the compounds of formula (I) which result from asymmetric centers, contained therein. Such isomers can be obtained in substantially pure form by classical separation techniques and by sterically controlled synthesis. Included is the specific case of the resolution of 1-ethyl-1,3,4,9-tetrahydro-4-(phenylmethyl)-pryrano[3,4-b]indole-1-acetic acid into its optical isomers by separation of the corresponding [(1S)-endo]-1,7,7-trimethyl-bicyclo[2.2.1]heptan-2-yl ester followed by basic hydrolysis.

ANTI-INFLAMMATORY ACTIVITY

The useful anti-inflammatory activities of the pyranoindole acetic acid derivatives of formula (I) are demonstrated in standard pharmacologic tests, for example, the test designated: Preventative Adjuvant Edema The objective of this test is to determine the ability of test drugs to exhibit an acute anti-inflammatory effect in rats. This test is a primary screen for anti-inflammatory drugs.

Species:

Male Sprague Dawley rats (180–200 g) are used. The animals have free access to water but food is withdrawn 18 hours before testing.

Drug Preparations and Administration:

Freund's complete adjuvant is prepared by suspending 5 mg of killed and dried *Mycobacterium butyricum* (Difco) in 1 mL mineral oil. The test compounds are dissolved, or suspended in 0.5% Tween 80 in distilled water according to their solubility. For primary screening all drugs are administered by gastric lavage at the arbitrary dosage of 25 mg/kg, p.o. in a volume of 0.5 mL/100 g body weight to groups of 10 animals.

Methodological Details:

The method is essentially that described by Wax et al, J. Pharmacol. Exp. Ther., 192, 166–171 (1975). Groups of rats are injected intradermally in the left hind paw with 0.1 mL of Freund's complete adjuvant. The test compound or vehicle is administered immediately before the adjuvant, 24 hours and 48 hours after the adjuvant (days 0, 1 and 2). The injected hind paw volume is measured before the injection of adjuvant and 24 hrs. after the last drug administration (day 3) by means of a plethysmometer (Buxco Electronics Inc.). The difference between the hind paw volume on day 0 and day 3 represents the edema volume. Etodolac (25 mg/kg, p.o.) is included as a positive control.

Presentation of Results:

The mean edema volume (expressed as mL±SEM) is calculated for each group and the percentage protection conferred by the drug is calculated:

$$\% \text{ protection} = \frac{(c - t) \, 100}{c}$$

where c is the mean edema volume for the vehicle-treated (0.5% Tween 80 in distilled water) controls and t is the mean edema volume for the drug treated group.

ANALGESIC ACTIVITY

A further test used to determine the utility of the compounds of the present invention is designated: Drug Effects of Phenylbenzoquinone-induced Writhing in Mice The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15–25 g). The animals are fasted for 18 hours prior to use but have free access to water.

Drug Preparation and Administration:

Drugs are dissolved or suspended according to their solubility in 0.5% Tween 80 in distilled water. They are administered by gastric gavage in a volume of 5 mL/kg. For primary screening all drugs are administered at the arbitrary dosage of 25 mg/kg, p.o. to a group of 10 mice.

Methodological Details:

A modification of the method of Siegmund et al, Proc. Soc. Exp. Biol. Med., 95, 729–731 (1957) is used. Groups of 5 mice are dosed with the test compound or vehicle control. Sixty minutes later the animals are injected i.p. with 0.3 mL/20 g body weight of a 0.02% solution of phenylbenzoquinone (PBQ; 2-phenyl-1,4-benzoquinone) and placed in individual observation boxes. The number of writhing or abdominal squirming movements is made by each mouse during the following 15 min. period is counted. The experiment is repeated with another group of 5 mice and the mean number of writhes per mouse for a group of 10 mice is calculated.

Presentation of Results:

Drug treated and vehicle-treated control groups are compared and the percentage protection conferred by the drug is calculated:

$$\text{Percentage protection} = \frac{(c - t) \, 100}{c}$$

where c = mean number of writhes in the control group
where t = mean number of writhes in the test drug group An additional test used to determine the utility of the compounds of the present invention is designated: Randall Selitto Test in the Rat The objective of this test is to assess the potency of peripheral and central acting drugs in inhibiting the reaction of rats to painful stimulation applied to an inflamed paw.

Species:

Male Sprague Dawley rats (180–200 g) are used. The animals are fasted overnight prior to drug administration.

Drug Preparation and Administration:

Freund's Complete Adjuvant (FCA) is prepared by suspending 5 mg killed and dried mycobacterium butyricum (Difco) in 1 mL mineral oil. The test compounds are dissolved or suspended in 0.5% Tween 80 in distilled water according to their solubility. They are administered by gastric gavage in a volume of 0.5 mL/100 g body weight to groups of 10 animals.

Methodological details:

Ten rats are used per group. The method is essentially that described by Randall and Selitto, Arch. Int. Pharmacodyn. 111, 409 (1957) and the apparatus which is used to apply pressure to the paw (Analgesi-meter for the rat paw, Ugo Basile, Comeria, Italy) is a modification of that described by Gilfoil et al, J. Pharmacol. 142, 1 (1963). The instrument is basically a device which exerts a force that increases at a constant rate. The force is continuously monitored by a pointer moving along a linear scale and is measured in grams. The inflammatory reaction is induced in the left hind paw of rats by injecting 0.1 mL of Freund's adjuvant intradermally. The test compound or vehicle is administered 24 hours after the adjuvant. The pain threshold (vocalization) is determined 1 hour later in the inflamed paw of the treated and control groups.

Presentation of Results and Criteria for Activity:

Each animal which has a reading 1.5 times greater than the mean reading of the control-group will be considered as responsive (having an analgesic effect) to treatment. The number of animals showing an analgesic effect is then determined in each group.

The $ED_{50}$ (dose which causes analgesia in 50% of the animals) using at least 3 doses is then determined, by the method described in Litchfield and Wilcoxon, J. Pharmacol. Exp. Ther., 96, 99–113 (1949).

Typical results obtained for the compounds of the present invention in the aforementioned tests are as follows:

TABLE I

Substituted 1,3,4,9-Tetrahydropyrano[3,4-b]indole-1-acetic Acids

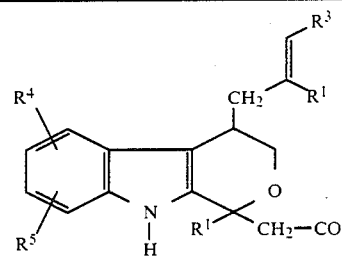

| Example | Preventative Adjuvant Edema* | Phenylquinone Writhing in Mice* | Randall Selitto Test in the Rat* |
|---|---|---|---|
| 1 | 37 | (1.9) | (0.003) |
| 2 | — | — | — |
| 3 | — | 19 | — |
| 4 | 15 | 86 | (0.5) |
| 5 | 4 | — | — |
| 6 | (3.2) | (18) | — |
| 7 | 37 | 15 | — |
| 10 | (7.8) | (7) | 60[b] |
| 11 | 55 | 11 | — |
| 12 | 32[a] | (9.5) | (1) |
| 13 | 36 | 2 | — |
| 14 | 46 | 21 | — |
| 15 | 30 | 25 | — |
| 16 | (3) | (5.5) | (0.012) |
| 17 | 44 | 11 | — |
| 18 | 15 | (3.2) | (0.8) |
| 19 | 52 | (3.3) | (1.6) |
| 20 | 34 | 11 | — |
| 21 | 40 | 11 | — |

TABLE I-continued
Substituted 1,3,4,9-Tetrahydropyrano[3,4-b]indole-1-acetic Acids

| Example | Preventative Adjuvant Edema* | Phenylquinone Writhing in Mice* | Randall Selitto Test in the Rat* |
|---|---|---|---|
| 22 | 47 | (4.7) | (0.25) |
| 23 | 0 | (1.4) | — |
| 24 | 2 | 0 | — |
| 25 | — | (3.1) | — |
| 26 | — | 10 | — |
| 27 | — | 24 | — |
| 29 | — | (3.2) | — |
| 34 | — | (1.4) | — |

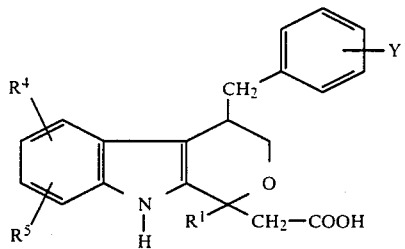

| | | | |
|---|---|---|---|
| 40 | 60 | 47 | — |
| 41 | — | 30 | — |
| 42 | 18$^a$ | 24$^a$ | — |
| 43 | 25$^a$ | 47$^a$ | — |
| 44 | 25$^a$ | 22$^a$ | — |
| 45 | 45$^a$ | 29$^a$ | — |

*The numbers quoted are either percent inhibition at 25 mg/kg or the ED$_{50}$ in mg/kg given in parentheses.
$^a$Tested at 10 mg/kg.
$^b$Tested at 5 mg/kg.

The lack of side effects associated with the compounds of this invention are demonstrated by standard acute toxicity tests as described by R. A. Turner in "Screening Methods in Pharmacology," Academic Press, New York and London, 1965, pp. 152–163, and by prolonged administration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula I of this invention will vary with the particular compound chosen and form of administration. Furthermore, it will vary with the particular host under treatment. Generally, the compounds of this invention are administered at a concentration level that affords efficacy without any deleterious side effects. These effective anti-inflammatory and analgesic concentration levels are usually obtained within a therapeutic range of 1.0 μg to 500 mg/kg per day, with a preferred range of 1.0 μg to 100 mg/kg per day. The preferred anti-inflammatory dose range is 1 mg to 20 mg/kg b.i.d. The preferred analgesic dose range is 1 μg to 4 mg/kg b.i.d.

The compounds of this invention may be administered in conjunction with nonsteroid anti-inflammatory drugs such as acetaminophen, ibuprofen and aspirin and/or with opiate analgesics such as codeine, oxycodone and morphine together with the usual doses of caffeine. When used in combination with other drugs, the dosage of the compounds of the present invention is adjusted accordingly.

The compounds of the present invention also possess antipyretic activity.

The following examples further illustrate this invention.

EXAMPLE 1

1-Ethyl-1,3,4,9-tetrahydro-4-(phenylmethyl)-pyrano[3,4-b]indole-1-acetic Acid (Isomer A)

(I, $R^1$=—$C_2H_5$, $R^2$ and $R^3$=—CH=CH—CH=CH—, $R^4$ and $R^5$=—H)

Step 1. Preparation of 3-Phenylpropionic Acid, Methyl Ester

A mixture of 3-phenylpropionic acid (118.2 g, 788 mmol) sulfuric acid (5.9 g), and 100 mL of methanol was heated to reflux overnight. TLC analysis indicated the absence of starting material and the reaction was concentrated in vacuo. The residue was dissolved in 200 mL of ethyl ether, washed with sodium bicarbonate (100 mL), dried over magnesium sulfate, filtered and concentrated to give 124.4 g (96.3%) of the ester as a tan oil.

IR (neat) 3020, 2940, 1730 cm$^{-1}$

Step 2. Preparation of β-(Phenylmethyl)-1H-indole-ethanol

To a solution of lithium diisopropylamine in tetrahydrofuran/cyclohexane (2.2 M, 136.4 mL, 300 mmol), cooled to −78° C. under a nitrogen atmosphere, was added a solution of 3-phenylpropionic acid, methyl ester (44.6 g, 272 mmol) (prepared in Step 1) in 150 mL of dry tetrahydrofuran. The mixture was allowed to stir for 30 minutes. A solution of isatin (20.0 g, 136 mmol) in 300 mL of tetrahydrofuran was added dropwise and the mixture was allowed to warm to room temperature for 3 hours. The mixture was quenched with 500 mL of saturated ammonium chloride and the layers were separated; the aqueous layer was washed with ether (2×150 mL). The combined organic extracts were dried over magnesium sulfate, filtered and concentrated to give 71.8 g of a brown oil. 3-Phenylpropionic acid, methyl ester was removed by distillation (95° C./1.5 mm) and the residue (50.6 g) was dissolved in 300 mL of dry tetrahydrofuran and added slowly to a cooled (0° C.) mixture of lithium aluminum hydride (18.56 g, 489 mmol) in 225 mL of tetrahydrofuran. The mixture was allowed to warm to room temperature and was then heated under reflux for 3 hours. The mixture was then cooled in an ice water bath, and 250 mL of water was slowly added. The salts were collected by filtration and washed with ether (3×400 mL). The organic layer was separated from the filtrate and dried over magnesium sulfate, filtered and concentrated to give 35.5 g of a red-brown oil. This material was purified by flash chromatography (30% ethyl acetate/hexane, silica gel) to give the tryptophol as a brown oil (16.02 g, 46.9%).

$^1$H NMR(CDCl$_3$) δ 8.08 (s, 1H), 7.65 (d, 1H, J=7.5 Hz), 7.36 (d, 1H, J=7.5 Hz), 7.18 (m, 7H), 7.01 (d, 1H, J=2.0 Hz), 3.84 (d, 2H, J=5.0 Hz), 3.43 (dt, 1H, J=7.5 Hz), 3.10 (d, 2H, J=8.0 Hz), 1.79 (s, 1H)

IR (neat) 3420, 3020 cm$^{-1}$

Step 3. Preparation of 1-Ethyl-1,3,4,9-tetrahydro-4-phenylmethyl)-pyrano[3,4-b]indole-1-acetic Acid, Methyl Ester A solution of β-(phenylmethyl)-1H-indole-ethanol (15.97 g, 63.6 mmol) (prepared in Step 2), methyl propionyl acetate (9.95 g, 76 mmol), and p-toluenesulfonic acid (1.60 g) in 500 mL of benzene was heated under reflux for 3 hours, and water collected with a Dean & Stark receiver. The reaction mixture was cooled to room temperature and washed with 5% aqueous sodium bicarbonate (200 mL), water (200 mL), dried over magnesium sulfate, filtered and concentrated to give 21.37 g of the crude product. The diastereomers were separated by flash chromatography (13% ethyl acetate/hexane, silica gel) to give Isomer A (higher Rf, 2.26 g, 9.8%) and Isomer B (lower Rf, 2.23 g, 9.8%) as yellow oils.

ISOMER A $^1$H NMR(CDCl$_3$) δ 9.17 (s, 1H), 7.42–7.00 (m, 9H), 3.80 (m, 2H), 3.72 (s, 3H), 3.20 (m, 2H), 3.01 (d, 1H, J=17 Hz), 2.80 (d, 1H, J=17 Hz), 2.85 (m, 1H), 2.05 (q, 2H, J=7.5 Hz), 0.90 (t, 3H, J=7.5 Hz)

IR (KBr) 3420, 1725 cm$^{-1}$

ISOMER B $^1$H NMR(CDCl$_3$) δ 8.88 (s, 1H), 7.38–7.00 (m, 9H), 3.84 (m, 2H), 3.70 (s, 3H), 3.04 (d, 1H, J=17.5 Hz), 2.78 (d, 1H, J=17.5 Hz), 3.15 (m, 2H), 2.82 (m, 1H), 2.20 (q, 2H, J=7.5 Hz), 0.82 (t, 3H, J=7.5 Hz)

IR (KBr) 3440, 1725 cm$^{-1}$

Step 4. Preparation of 1-Ethyl-1,3,4,9-tetrahydro-4-(phenylmethyl)-pyrano[3,4-b]indole-1-acetic Acid 1-Ethyl-4-(phenylmethyl)-1,3,4,9-tetrahydropyrano(3,4-b)indole-1-acetic acid, methyl ester Isomer A (prepared in Step 3) (3.0 g, 8.25 mmol) was dissolved in 100 mL of ethanol, and 100 mL of 10% aqueous sodium hydroxide was added. The mixture was heated under reflux for 2 hours, and was then concentrated to a cloudy aqueous solution. Concentrated hydrochloric acid was added until the mixture was acidic. It was then washed with ether (2×100 mL) and the combined ether extracts were dried over magnesium sulfate, filtered and concentrated to give 2.8 g of an off-white foam. This material was recrystallized from benzene/petroleum ether to give 2.30 g (80%) of the pure acid as a white solid, m.p. 144–146° C.

$^1$H NMR(CDCl$_3$) δ 8.70 (s, 1H), 7.43–7.03 (m, 9H), 3.87 (d, 2H, J=2.5 Hz), 3.23 (m, 2H), 2.97 (d, 2H, J=3.0 Hz, 2.85 (m, 1H), 2.04 (m, 2H), 0.93 (t, 3H, J=7.5 Hz)

IR (KBr) 3380, 3260, 1740 cm$^{-1}$

Anal. Calcd. for C$_{22}$H$_{23}$NO$_3$: C, 75.62; H, 6.63; N, 4.01. Found: C, 75.96; H, 6.43; N, 3.99.

Preparation of 1-Ethyl-1,3,4,9-tetrahydro-4-(phenylmethyl)-pyrano[3,4-b]indole-1-acetic Acid, Sodium Salt (Isomer A)

Aqueous NaOH (2.6 mL of 1N solution) was added to a stirred solution of 1-ethyl-1,3,4,9-tetrahydro-4-(phenylmethyl)pyrano[3,4-b]indole-1-acetic acid (0.965 g, 2.76 mmol) in methanol (50 mL). The pH was adjusted to 7.75 by the portionwise addition of 1-ethyl-1,3,4,9-tetrahydro-4-(phenylmethyl)-pyrano[3,4-b]indole-1-acetic acid. The resulting solution was evaporated to dryness and then taken into benzene and evaporated (2×). The residue was dissolved in ethyl acetate (8 mL), stirred, and petroleum ether (30–60°, 30 mL) was added slowly. The precipitate which formed was stirred for 1 hour, filtered, washed with petroleum ether, and dried to afford 1.0 g (98%) of the salt as a white solid, m.p. 180–190° C. (dec.).

| NMR (DMSO-d$_6$): | | |
|---|---|---|
| No. of protons | Type | Chemical Shift (δ) |
| 3 | CH$_3$ | 0.84 (t, J = 8) |
| 2 | CH$_2$ | 2.0 (2q, J = 8) |
| 7 | 3CH$_2$.CH | 2.2–3.9 (m) |
| 9 | aromatic | 6.9–7.2 (m) |

Anal. Calcd.: C, 7.14; H, 5.97; N, 3.77%. Found: C, 70.41; H, 6.03; N, 3.64%.

EXAMPLE 2

1-Ethyl-1,3,4,9-tetrahydro-4-(phenylmethyl)-pyrano[3,4-b]-indole-1-acetic Acid, Methyl Ester (Isomer A)

Step 1. Preparation of Indole-3-acetic Acid, Methyl Ester

Indole-3-acetic acid (25 g, 143 mmol) was dissolved in 500 mL of methanol and 5 mL of concentrated sulfuric acid was added. The resulting solution was heated under reflux overnight. TLC analysis indicated the absence of starting material and the reaction mixture was concentrated in vacuo. The residue was dissolved in 300 mL of ethyl ether, washed with 5% aqueous sodium bicarbonate (2×150 mL), dried over magnesium sulfate, filtered and concentrated to 24.09 g (89.1%) of the ester as a burgandy colored oil.

IR (neat) 3400, 1720 cm$^{-1}$

NMR(CDCl$_3$) δ 8.17 (s, 1H), 7.62 (d, 1H, J=6.7 Hz), 7.32–7.07 (m, 4H), 3.79 (s, 3H), 3.70 (s, 3H)

Step 2. Preparation of α-(Phenylmethyl)-1H-indole-3-acetic Acid, Methyl Ester

To a 2-liter three necked round bottom flask equipped with an addition funnel was added, under nitrogen, 300 mL of dry tetrahydrofuran (THF) and 68.75 mL of lithium disopropylamide (1.92M in cyclohexane/THF, 132 mmol). The mixture was cooled to −78° C., and a solution of indole-3-acetic acid, methyl ester (11.36 g, 60 mmol) in 300 mL of dry tetrahydrofuran was added dropwise. The mixture was then allowed to sit at −78° C. for 15 minutes, and then a solution of benzyl chloride (7.59 g, 60 mmol) in 300 mL of tetrahydrofuran was added dropwise. The reaction mixture must be stirred vigorously so that the precipitated dianion of indole-3-acetic acid, methyl ester reacts completely with the benzyl chloride. After 3 hours, TLC analysis indicated complete consumption of starting material, and 200 mL of aqueous saturated ammonium chloride was added. The aqueous layer was separated and washed with ether (2×100 mL). The combined ether extracts were added to the organic layer which was dried over magnesium sulfate, filtered and concentrated to 15.0 g (quantitative yield) of red-brown oil. This material was reduced to the corresponding tryptophol without further purification.

$^1$H NMR(CDCl$_3$) δ 8.09 (s, 1H), 7.73 (d, 1H, J=7 Hz), 7.40–7.09 (m, 9H), 4.19 (dd, 1H), 3.59 (s, 3H), 3.47 (dd, 1H), 3.20 (dd, 1H),

IR (neat) 3400, 1730 cm$^{-1}$

Step 3. Preparation of β-(Phenylmethyl)-1H-indoleethanol

The crude α-(phenylmethyl)-1H-indole-3-acetic acid, methyl ester obtained in Step 2 (15 g, 60 mmol) was dissolved in 100 mL of dry tetrahydrofuran and added dropwise to a cooled suspension of lithium aluminum hydride (2.73 g, 72 mmol) in 300 mL of tetrahydrofuran. The mixture was allowed to warm to room temperature and was then refluxed for 1.5 hours (heating is usually not required in this reaction). The mixture was cooled in an ice water bath and 150 mL of 1N hydrochloric acid was added dropwise. The aqueous layer was removed and the organic layer was washed with saturated sodium bicarbonate (2×100 mL), dried over magnesium sulfate, filtered and evaporated to produce 15.06 g (quantitative yield) of a brown oil having the same physical properties as the product obtained in Example 1, Step 2. This material was cyclized to the pyranoindole in Step 4 without further purification.

Step 4. Preparation of 1-Ethyl-1,3,4,9-tetrahydro-4-(phenylmethyl)pyrano[3,4-b]indole-1-acetic Acid, Methyl Ester The crude β-(phenylmethyl)-1H-indole-ethanol obtained in Step 3 (15.06 g, 60 mmol) was dissolved in 250 mL of methylene chloride. 3-Methoxy-2-pentenoic acid, methyl ester (10.68 g, 72 mmol) was added followed by 2.5 mL of boron trifluoride etherate and the mixture was allowed to stir at room temperature overnight. TLC analysis indicated that the reaction was complete and 200 mL of saturated sodium bicarbonate was added. The organic layer was separated and washed with water (2×100 mL), dried over magnesium sulfate, filtered and concentrated to give a crude product which was purified by flash chromatography (13% ethyl acetate/hexane, silica gel). 2.5 g (11.5% based on 3 steps) of almost pure Isomer A was obtained. The proton NMR of this compound matched that of the sample prepared by the procedure described in Example 1, Step 3.

EXAMPLE 3

1-Ethyl-1,3,4,9-tetrahydro-4-(phenylmethyl)-pyrano[3,4-b]indole-1-acetic Acid (Isomer B)

(I, $R^1=-C_2H_5$, $R^2$ and $R^3=-CH=CH-CH=CH-$, $R^4$ and $R^5=-H$)

The 1-ethyl-1,3,4,9-tetrahydro-4-(phenylmethyl)-pyrano[3,4-b]-indole-acetic acid, methyl ester Isomer B, (prepared in Example 1, Step 3) (2.19 g, 6.0 mmol) was added to a mixture of 65 mL of 10% aqueous sodium hydroxide and 65 mL of ethanol and the reaction mixture was heated under reflux for 2 hours. The mixture was then concentrated to dryness and a 1:1 mixture of 10% sodium hydroxide/ether was added to the residue. The aqueous layer was separated, acidified with concentrated hydrochloric acid, and extracted several times with ether. The combined ether extracts were dried over magnesium sulfate, filtered and concentrated to give 1.68 g (80%) of a tan-yellow solid. This material was purified by flash chromatography (30% ethyl acetate/hexane, silica gel) to give 410 mg of material which was recrystallized from benzene/petroleum ether to give 315 mg (15%) of the acid as a white solid, m.p. 171°–173° C.

$^1$H NMR(CDCl$_3$) δ 8.48 (s, 1H), 7.39–7.01 (m, 9H), 3.90 (dd, 2H, J=7.5 Hz, J=2.5 Hz), 3.19 (m, 2H), 3.02 (d, 2H, J=3 Hz), 2.88 (m, 1H), 2.15 (m, 2H), 0.89 (t, 3H, J=7.5 Hz)

IR(KBr) 3390, 1722 cm$^{-1}$

Anal. Calcd. for $C_{22}H_{23}NO_3$: C, 75.62; H, 6.63; N, 4.01. Found: C, 75.76; H, 6.35; N, 3.95.

EXAMPLE 4

1,8-Diethyl-1,3,4,9-tetrahydro-4-(phenylmethyl)-pyrano[3,4-b]indole-1-acetic Acid (I, $R^1=-C_2H_5$, $R^2$ and $R^3=-CH=CH-CH=CH-$, $R^4=-H$, $R^5=8-C_2H_5$)

Step 1. Preparation of 1-(7-Ethyl-1H-indol-3-yl)-3-phenylpropanone

To a vigorously stirred solution of ethyl magnesium bromide (2.85M in ether, 0.07 mol, 24.6 mL) in anhydrous ether (50 mL), was added a solution of 7-ethyl-1H-indole (7.25 g, 0.05 mol) in benzene (25 mL), dropwise over the course of 10 minutes. The resulting pale green mixture was heated at reflux for 2 hours, and then cooled to −10° C. with a dry ice/methanol bath. A solution of hydrocinnamoyl chloride (8.43 g, 0.05 mol) in benzene (20 mL) was added dropwise (45 minutes). The reaction mixture was allowed to warm to room temperature; after an additional 2 hours, no starting material was detected by TLC analysis. Aqueous ammonium chloride (10%, 30 mL) was added to the reaction mixture and a white precipitate formed, which was collected by filtration, washed with ether, and dried in vacuo to yield 7.78 g (56%) of the desired ketone, m.p. 140°–141.5° C.

IR(CHCl$_3$) 3465, 1645 cm$^{-1}$

NMR(CDCl$_3$) δ 9.39 (s, 1H), 8.30 (d, 1H), 7.80 (d, 1H), 3.12 (s, 4H), 2.88 (q, 2H), 1.32 (t, 3H)

Step 2. Preparation of 7-Ethyl-α-(phenylmethyl)-1H-indole-3-acetic Acid Methyl Ester According to the procedure of E. C. Taylor et al, J. Amer. Chem. Soc., 98, 3037 (1976), a solution of 1-(7-ethyl-1H-indol-3-yl)-3-phenylpropanone (2.77 g, 10 mmol) in a 1:1 mixture of methanol and trimethylorthoformate (25 mL) was added to thallium (III) nitrate trihydrate (4.88 g, 11 mmol), and the mixture was heated under reflux until precipitation of thallium (I) nitrate was complete (about 3 hours). The dark brown mixture was diluted with 25 mL of ether, and the thallium (I) nitrate was removed by filtration. The filtrate was washed successively with 1×50 mL portions of water, 5% aqueous sodium bicarbonate, and water and was then dried over anhydrous MgSO$_4$. Concentration of the filtrate and flash chromatography of the crude product (20% ethyl acetate/hexane, silica gel) gave the ester as a red-brown oil (0.98 g, 31.9%).

IR(CHCl$_3$) 3485, 1735 cm$^{-1}$

NMR(CDCl$_3$) δ 8.35 (s, 1H), 7.70 (dd, 1H), 7.15 (m, 3H), 4.28 (m, 1H), 3.75 (s, 3H), 3.35 (s, 3H), 2.80 (q, 2H), 1.25 (m, 3H)

Step 3. Preparation of 7-Ethyl-β-(phenylmethyl)-1H-indole-ethanol

To a stirred suspension of lithium aluminum hydride (0.702 g, 18.5 mmol) in 80 mL of anhydrous tetrahydrofuran under nitrogen at 0° C. was slowly added (about 1.5 hours) a solution of 7-ethyl-α-(phenylmethyl)-1H-indole-3-acetic acid methyl ester (prepared in Step 2) (5.17 g, 16.8 mmol) in 30 mL of anhydrous tetrahydrofuran. The resulting dark red mixture was heated under reflux for 2 hours. It was cooled to 0° C., and quenched by the dropwise addition of 40 mL of water. The precipitated aluminum salts were removed by filtration and washed with ether. The layers of the filtrate were separated, and the aqueous layer was washed with ether. The combined ether layers were washed with saturated sodium chloride, dried over anhydrous magnesium sulfate, and concentrated to give the desired alcohol as a brown oil (4.51 g, 96%).

IR(CHCl₃) 3570, 3480 cm$^{-1}$
NMR(CDCl₃) δ 6.8–8.40 (m, 10H), 3.0–4.10 (m, 5H), 2.80 (q, 2H), 1.32 (t, 3H)

Step 4. Preparation of 1,8-Diethyl-1,3,4,9-tetrahydro-4-(phenylmethyl)pyrano[3,4-b]indole-1-acetic Acid (Isomer A)

7-Ethyl-β-(phenylmethyl)-1H-indole-ethanol (prepared in Step 3) (5.86 g, 21.0 mmol), methyl propionyl acetate (4.69 g, 36.0 mmol) and p-toluenesulfonic acid (0.49 g, 2.6 mmol) were dissolved in 175 mL of benzene and heated under reflux for 5 hours, and water collected with a Dean & Stark receiver. The mixture was washed with saturated sodium bicarbonate (2×50 mL), dried (MgSO₄), filtered and evaporated to give the crude methyl ester. This material was dissolved in a mixture of 125 mL of ethanol and 125 mL of 10% aqueous sodium hydroxide, and the mixture was heated under reflux for 2½ hours. It was then concentrated to dryness, and a mixture of 100 mL of ether and 50 mL of 10% aqueous sodium hydroxide was added to the residue. The layers were separated, and the aqueous layer was acidified with concentrated hydrochloric acid and extracted with ether (2×100 mL). The combined ether extracts were dried over anhydrous MgSO₄, filtered and evaporated to give the crude product as a tan solid (44% yield). The diastereomers were partially separated by flash chromatography (30% ethyl acetate/hexane, H₃PO₄ treated silica gel), and a portion of the mixed fractions from the column were separated by HPLC (Waters Assoc. C18, Prep 500). The isomer which eluted first on the C18 column was designated Isomer A and had a m.p. 147°–148.5° C.; the other isomer was designated Isomer B and had a m.p. 158°–159.5° C. Each isomer was recrystallized from 1:3 benzene/petroleum ether.

ISOMER A

IR(KBr) 3600–2600, 3330, 1740 cm$^{-1}$. Analytical HPLC: 97.98% isomeric purity.

Anal. Calcd. for C₂₄H₂₇NO₃: C, 76.35; H, 7.22; N, 3.71. Found: C, 76.28; H, 7.25; N, 3.81.

EXAMPLE 5

1,8-Diethyl-1,3,4,9-tetrahydro-4-(phenylmethyl)-pyrano[3,4-b]indole-1-acetic Acid (Isomer B)

ISOMER B

Prepared in Example 4, Step 4.

IR(KBr) 3600–2600, 3460, 1700 cm$^{-1}$. Analytical HPLC: 96.90% isomeric purity.

Anal. Calcd. for C₂₄H₂₇NO₃: C, 76.35; H, 7.22; N, 3.71. Found: C, 76.28; H, 7.25; N, 3.81.

EXAMPLE 6

1-Ethyl-7-fluoro-1,3,4,9-tetrahydro-8-methyl-4-(2-propenyl)pyrano[3,4,-b]indole-1-acetic Acid (Isomer A)

(I, R$^1$=—C₂H₅, R$^2$ and R$^3$=—H, R$^4$=7—F, R$^5$=8—CH₃)

Step 1. Preparation of 6-Fluoro-7-methylisatin

A mixture consisting of 3-fluoro-2-methyl aniline hydrochloride (21.9 g), water (500 mL), hydroxylamine hydrochloride (29 g), sodium sulfate (120 g) and a few drops of 6N HCl was heated to boiling with vigorous stirring. To this was added a boiling solution of chloral hydrate (21.9 g in 330 mL of water) and boiling continued for 45 minutes.

The reaction was cooled and filtered. The precipitate was dissolved in ether, dried over sodium sulfate and evaporated to afford 18.7 g of the oxime (88% yield).

The oxime was added portionwise to 300 mL of 90% sulfuric acid at 65° C. The mixture was heated to 80° C. for 15 minutes and then poured over ice water while stirring. Filtration and drying afforded 11.7 g (60% yield) of 6-fluoro-7-methylisatin, m.p. 204°–206° C.

Step 2. Preparation of 6-Fluoro-7-methylindole-3-(2-allyl)ethanol

A solution of lithium diisopropylamine (LDA) (2.2M in cyclohexane, 110 mL) was cooled to −78° C. in an isopropylamine (IPA) dry ice bath. Methyl 4-pentenoate (24.0 g, 0.206 mol) in dry tetrahydrofuran (100 mL) was introduced, and the reaction stirred for 0.5 hours. A solution of 6-fluoro-7-methylisatin (prepared in Step 1) (19 g, 0.106 mol) in tetrahydrofuran (150 mL) containing 2-methylpyrrolidone (22 mmol) was added slowly while keeping the temperature of the reaction below −60° C. The reaction was stirred at −78° C. for 2 hours and then allowed to reach room temperature. The excess LDA was quenched using saturated ammonium chloride solution. The organic layer was extracted with ether (2×200 mL), dried (Na₂SO₄) and concentrated to afford 40.0 g of crude intermediate hydroxyester.

A solution of this hydroxyester intermediate in tetrahydrofuran (500 mL) was added dropwise to a stirred suspension of LiAlH₄ (9.8 g, 0.258 mol) in tetrahydrofuran (200 mL), and refluxed for 2 hours. The reaction was cooled in an ice bath, the excess hydride destroyed using 1:1 tetrahydrofuran/H₂O, filtered, dried (Na₂SO₄) and concentrated to give 30 g of crude tryptophol. Flash chromatography using 25% ethyl acetate/hexane followed by 30% ethyl acetate/hexane afforded 11.7 g (48% yield) of title compound. This material was immediately used in Step 3.

Step 3. Preparation of 1-Ethyl-7-fluoro-1,3,4,9-tetrahydro-8-methyl-4-(2-propenyl)-pyrano[3,4-b]indole-1-acetic Acid (Isomer A)

A mixture consisting of 6-fluoro-7-methylindole-3-(2-allyl)ethanol (prepared in Step 2) (11.0 g, 0.048 mol), 3-methoxy-2-pentenoic acid, methyl ester (11 g), BF₃.Et₂O (1 mL) and dichloromethane (500 mL) was stirred at room temperature for 2 hours, diluted with dichloromethane, washed with 5% NaHCO₃, water, dried (MgSO₄) and concentrated to give 21 g of oil. This was washed through a silica gel column using hexane followed by 5% ethyl acetate-hexane. Preparative liquid chromatography on a Waters Assoc. Prep 500 instrument using 3.5% ethyl acetate-hexane as eluant afforded the esters (5 g of Isomer A and 6.5 g of Isomer B).

Isomer A ester was hydrolyzed by refluxing with a mixture of KOH (5 g), methanol (500 mL), and water (10 mL) for 2.5 hours. The reaction was concentrated, diluted with water, and extracted with ether. The aqueous phase was acidified with 5% HCl and extracted with chloroform (3×200 mL). The combined extracts were washed with water, dried (MgSO₄) and concentrated to give 3 g of solid acid. Recrystallization from toluene-petroleum ether afforded 2.0 g (12.6% yield) of title compound, m.p. 159°–160° C.

| NMR (DMSO-d₆): | | |
|---|---|---|
| No. of Protons | Type | Chemical Shift (δ) |
| 3 | CH₃ | 0.72 (t, J = 7) |
| 2 | CH₂ | 1.95 (m) |

-continued

| | NMR (DMSO-d₆): | |
|---|---|---|
| No. of Protons | Type | Chemical Shift (δ) |
| 3 | CH₃ | 2.35 (s) |
| 2 | =CH₂ | 5.1 (m) |
| 1 | H—C=C | 5.8 (m) |
| 2 | aromatic | 10.6, 11.9 (s) |

IR(KBr, cm⁻¹) 3070 (NH/OH), 1710 (CO)
Anal. Calcd.: C, 68.87; H, 6.69; N, 4.23%. Found: C, 68.94; H, 6.61; N, 4.15%.

EXAMPLE 7

1-Ethyl-7-fluoro-1,3,4,9-tetrahydro-8-methyl-4-(2-propenyl)pyrano[3,4-b]indole-1-acetic Acid (Isomer B)

1-Ethyl-7-fluoro-1,3,4,9-tetrahydro-8-methyl-4-(2-propenyl)pyrano[3,4-b]indole-1-acetic acid Isomer B ester, prepared in Example 6, Step 3, was hydrolyzed as described in Example 6, Step 3, to afford 2.1 g of white solid. Recrystallization from toluene-petroleum ether afforded 1.3 g (8.1% yield) of title compound, m.p. 138°–140° C.

| | NMR (DMSO-d₆): | |
|---|---|---|
| No. of Protons | Type | Chemical Shift (δ) |
| 3 | CH₃ | 0.62 (t, J = 7) |
| 1 | CH₃ | 2.35 (s) |
| 2 | CH₂ | 2.06 (m) |
| 2 | =CH₂ | 5.1 (m) |
| 1 | H—C=C | 5.8 (m) |
| 2 | aromatic | 10.6, 11.9 (s) |

IR(KBr, cm⁻¹) 3070 (NH/OH), 1710 (CO)
Anal. Calcd.: C, 68.87; H, 6.69; N, 4.23%. Found: C, 68.98; H, 6.77; N, 4.18%.

EXAMPLE 8

Resolution of
(+/−)-1-Ethyl-1,3,4,9-tetrahydro-4-(phenylmethyl)-pyrano[3,4-b]indole-1-acetic Acid Step 1. Preparation of 1-Ethyl-1,3,4,9-tetrahydro-4-(phenylmethyl)pyrano[3,4-b]indole-1-acetic Acid, [(1S)-Endo]-1,7,7-Trimethyl-bicyclo[2.2.1]heptan-2-yl Ester 50 mL of methylene chloride was added to a mixture of 1-ethyl-1,3,4,9-tetrahydro-4-(phenylmethyl)-pyrano[3,4-b]indole-1-acetic acid (3.50 g, 10 mmol), [(1S)-endo]-(−)-borneol (1.70 g, 11 mmol), 1,3-dicyclohexylcarbodiimide (2.27 g, 11 mmol) and 4-(N,N-dimethylamino)pyridine (70 mg, 0.57 mmol). The mixture was allowed to stir at room temperature overnight under a stream of nitrogen. The mixture was passed through a sintered glass funnel and the precipitate was washed with 50 mL of methylene chloride. The filtrate was poured into 100 mL of ether and was washed with 1N hydrochloric acid (2×50 mL) and saturated sodium bicarbonate (1×50 mL), dried over magnesium sulfate, filtered and concentrated to give 3.85 g of the crude mixture of esters. Flash chromatography (10% ethyl acetate/hexane, silica gel) gave 2.65 g of the diastereomeric mixture of esters as a white foam. The esters were separated by HPLC (Waters Prep. 500A, 4% ethyl acetate/hexane, silica gel) to give 1.2 g of Isomer A (first eluting isomer) m.p. 63°–66° C., and 1.15 g of Isomer B (second eluting isomer) m.p. 58°–61° C.

Step 2. Preparation of (+)-1-Ethyl-1,3,4,9-tetrahydro-4-(phenylmethyl)pyrano[3,4-b]indole-1-acetic Acid The 1-ethyl-1,3,4,9-tetrahydro-4-(phenylmethyl)-pyrano[3,4-b]indole-1-acetic acid, [(1S)-endo]-1,7,7-trimethyl-bicyclo[2.2.1]heptan-2-yl ester (Isomer A, 1.20 g, 2.5 mmol) was dissolved in a mixture of 65 mL of ethanol and 65 mL of 10% sodium hydroxide, and the mixture was heated under reflux for 5 hours. The mixture was then concentrated to a cloudy aqueous solution, cooled in an ice water bath, and acidified with concentrated hydrochloric acid. It was then extracted with ether (2×50 mL) and the combined ether extracts were dried over magnesium sulfate, filtred and concentraed to give 900 mg of a yellow oil. This material was recrystallized from toluene to give 397 mg (46%) of the pure acid as a white solid, m.p. 170°–171.5° C.

Anal. Calcd. for C₂₂H₂₃NO₃: C, 75.62; H, 6.63; N, 4.01. Found: C, 75.63; H, 6.44; N, 4.17.
[α]$_D^{25}$ = +62.9°

EXAMPLE 9

Preparation of (−)-1-Ethyl-1,3,4,9-tetrahydro-4-(phenylmethyl)-pyrano[3,4-b]indole-1-acetic Acid 1-Ethyl-1,3,4,9-tetrahydro-4-(phenylmethyl)-pyrano[3,4-b]indole-1-acetic acid, [(1S)-endo]-1,7,7-trimethyl-bicyclo[2.2.1]heptan-2-yl ester, Isomer B, prepared in Example 8, Step 1, was saponified as described in Example 2, Step 2, to give 327 mg (41.3%) of the pure acid as a white solid, m.p. 171°–172° C.

Anl. Calcd. for C₂₂H₂₃NO₃: C, 75.62; H, 6.63; N, 4.01. Found: C, 75.55; H, 6.42; N, 4.31.
[α]$_D^{25}$ = −60.3°

TABLE II

Substituted 1,3,4,9-Tetrahydropyrano[3,4-b]indole Acetic Acids

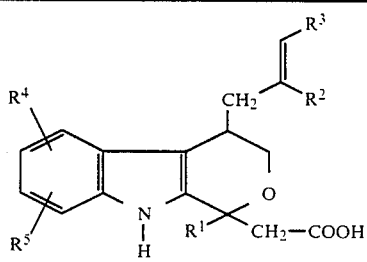

| Example | R¹ | R² | R³ | R⁴ | R⁵ | Isomer | Melting Point °C. |
|---|---|---|---|---|---|---|---|
| 1 | Et | CH=CH—CH=CH | | H | H | A | 145–147 |
| 2 | Et | CH=CH—CH=CH | | H | H | A | — |
| 3 | Et | CH=CH—CH=CH | | H | H | B | 171–173 |

TABLE II-continued

Substituted 1,3,4,9-Tetrahydropyrano[3,4-b]indole Acetic Acids

| | | | | | | | |
|---|---|---|---|---|---|---|---|
| 4 | Et | CH=CH—CH=CH | | H | 8-$C_2H_5$ | A | 147–148.5 |
| 5 | Et | CH=CH—CH=CH | | H | 8-$C_2H_5$ | B | 158–159.5 |
| 6 | Et | H | H | 7-F | 8-$CH_3$ | A | 159–160 |
| 7 | Et | H | H | 7-F | 8-$CH_3$ | B | 138–140 |
| 8 | Et | CH=CH—CH=CH | | H | H | A(+) | 170–171.5 |
| 9 | Et | CH=CH—CH=CH | | H | H | A(−) | 171–172 |
| 10 | Et | H | H | 7-F | 8-$C_2H_5$ | A | 91–93.5 |
| 11 | Et | H | H | H | 8-$C_2H_5$ | B | 118–119.5 |
| 12 | Et | H | H | H | 8-n-$C_3H_7$ | A | 99.5–101.5 |
| 13 | Et | H | H | H | 8-n-$C_3H_7$ | B | 117–120 |
| 14 | Et | H | H | H | H | A | 133–138 |
| 15 | Et | H | H | H | H | B | 136–141 |
| 16 | Et | H | H | 7-Cl | 8-$CH_3$ | A | 168–169 |
| 17 | Et | H | H | 7-Cl | 8-$CH_3$ | B | 124–126 |
| 18 | Et | CH=CH—CH=CH | | 7-Cl | 8-Cl | A | 154–155 |
| 19 | Et | CH=CH—CH=CH | | 7-Cl | 8-$CH_3$ | A | 158–159 |
| 20 | Et | CH=CH—CH=CH | | 7-Cl | 8-$CH_3$ | B | 218–220 |
| 21 | Et | CH=CH—CH= | | H | 8-$CH_3$ | B | 174–176 |
| 22 | Et | CH=CH—CH=CH | | H | 8-$CH_3$ | A | 141–143 |
| 23 | Et | CH=CH—CH=CH | | 5-$CH_3$ | 8-Cl | A | 151–152 |
| 24 | Et | CH=CH—CH=CH | | 5-$CH_3$ | 8-Cl | B | 250–252 |
| 25 | Et | CH=CH—CH=CH | | 6-Br | H | A | 154–155.5 |
| 26 | Et | CH=CH—CH=CH | | 6-Br | H | B | 156–158.5 |
| 27 | Et | H | H | 6-F | H | B | 145–147 |
| 28 | Et | CH=CH—CH=CH | | 6-F | H | B | 190–192 |
| 29 | Et | CH=CH—CH=CH | | 5-Cl | 8-$CH_3$ | A | 172–173 |
| 30 | Et | CH=CH—CH=CH | | 5-Cl | 8-$CH_3$ | B | 248–250 |
| 31 | Propyl | CH=CH—CH=CH | | H | H | A | 139.5–141 |
| 32 | Propyl | CH=CH—CH=CH | | H | H | B | 172–173 |
| 33 | Et | CH=CH—CH=CH | | H | 7-Cl | B | 186.5–188 |
| 34 | Et | CH=CH—CH=CH | | H | 7-Cl | A | 152.5–154 |
| 35 | Et | CH=CH—CH=CH | | 5-$CH_3$ | 8-$CH_3$ | A | 175–177 |
| 36 | Et | CH=CH—CH=CH | | 5-$CH_3$ | 8-$CH_3$ | B | 230–232 |
| 37 | Et | H | H | H | 8-$CH_3$ | A | 135–137 |
| 38 | Et | H | H | H | 8-$CH_3$ | B | 138–139 |
| 39 | Methyl | CH=CH—CH=CH | | H | H | A | 157–158 |

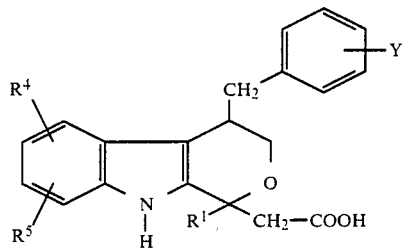

| Example | $R^1$ | Y | $R^4$ | $R^5$ | Isomer | Melting Point °C. |
|---|---|---|---|---|---|---|
| 40 | $C_2H_5$ | 4-Cl | H | H | A | 182–184 |
| 41 | $C_2H_5$ | 4-$OCH_3$ | H | H | B | 163.5–164.5 |
| 42 | $C_2H_5$ | 4-Cl | H | H | B | 187.5–190 |
| 43 | $C_2H_5$ | 4-F | H | H | A | 126–128 |
| 44 | $C_2H_5$ | 3-$CF_3$ | H | H | B | 164.5–166 |
| 45 | $C_2H_5$ | 2,4-diF | H | H | A | 150–151.5 |

We claim:

1. The compounds having the structure

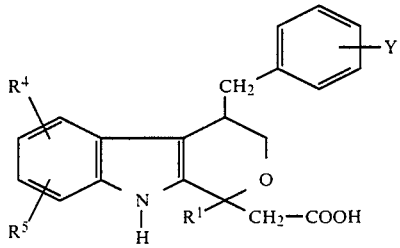

(XIV)

wherein $R^1$ is lower alkyl containing 1 to 4 carbon atoms, $R^4$ and $R^5$ are hydrogen, alkyl containing 1 to 6 carbon atoms or halogen, and Y is 4-halogen, 2- and 4-dihalogen, 3-trifluoromethyl or 4-methoxy and the pharmaceutically acceptable salts thereof.

2. A pharmaceutical composition for treating inflammatory conditions and for producing analgesia in a mammal comprising an effective amount of a compound of structure (XIV), or a pharmaceutically acceptable salt thereof, as claimed in claim 1 and a pharmaceutically acceptable carrier.

3. A method for treating inflammatory conditions and for producing analgesia in a mammal which comprises the administration to said mammal of an effective amount of a compound selected from those of formula (XIV), or a pharmaceutically acceptable salt thereof, as claimed in claim 1.

* * * * *